(12) United States Patent
Alexander et al.

(10) Patent No.: US 6,984,834 B2
(45) Date of Patent: Jan. 10, 2006

(54) RADIATION SOURCE MODULE

(75) Inventors: James C. Alexander, London (CA); Michael A. Plaisier, Dorchester (CA); Michael P. Sarchese, Belmont (CA)

(73) Assignee: Trojan Technologies Inc. (CA)

( * ) Notice: Subject to any disclaimer, the term of this patent is extended or adjusted under 35 U.S.C. 154(b) by 249 days.

(21) Appl. No.: 10/846,592

(22) Filed: May 17, 2004

(65) Prior Publication Data

US 2004/0211926 A1 Oct. 28, 2004

Related U.S. Application Data

(63) Continuation of application No. 09/493,226, filed on Jan. 28, 2000, now abandoned.

(51) Int. Cl.
*G01N 21/51* (2006.01)
*B01J 19/12* (2006.01)

(52) U.S. Cl. .................. 250/493.1; 250/431; 422/186.3
(58) Field of Classification Search .............. 250/493.1, 250/431; 422/186.3
See application file for complete search history.

(56) References Cited

U.S. PATENT DOCUMENTS

| | | | | |
|---|---|---|---|---|
| 2,413,704 A | * | 1/1947 | Glatthar et al. | 250/435 |
| 5,019,256 A | * | 5/1991 | Ifill et al. | 210/232 |
| 5,590,390 A | * | 12/1996 | Maarschalkerweerd | 422/186.3 |
| RE36,896 E | * | 10/2000 | Maarschalkerweerd | 422/186.3 |
| 6,231,820 B1 | * | 5/2001 | Wedekamp | 422/186.3 |
| 6,507,028 B2 | * | 1/2003 | Sarchese et al. | 250/436 |

* cited by examiner

*Primary Examiner*—John R. Lee
*Assistant Examiner*—Anthony Quash
(74) *Attorney, Agent, or Firm*—Katten Muchin Zavis Rosenman

(57) ABSTRACT

The present invention provides a radiation source module for use in a fluid treatment system. In one embodiment, the module comprises: a substantially elongate first support member having a longitudinal first axis; and a first pair of radiation source assemblies extending from the first support member, each radiation source assembly comprising a radiation source; wherein the first pair of radiation source assemblies is oriented such that a second axis extending through a center point of each radiation source assembly is disposed at an angle with respect to the first axis. In another embodiment, the module comprises a substantially elongate first support member having a longitudinal first axis; and a first column of radiation source assemblies extending from the first support member, and a second column of radiation source assemblies extending from the first support member, each radiation source assembly comprising a radiation source; the first column of radiation source assemblies and the second column of radiation source assemblies disposed adjacent one another.

45 Claims, 8 Drawing Sheets

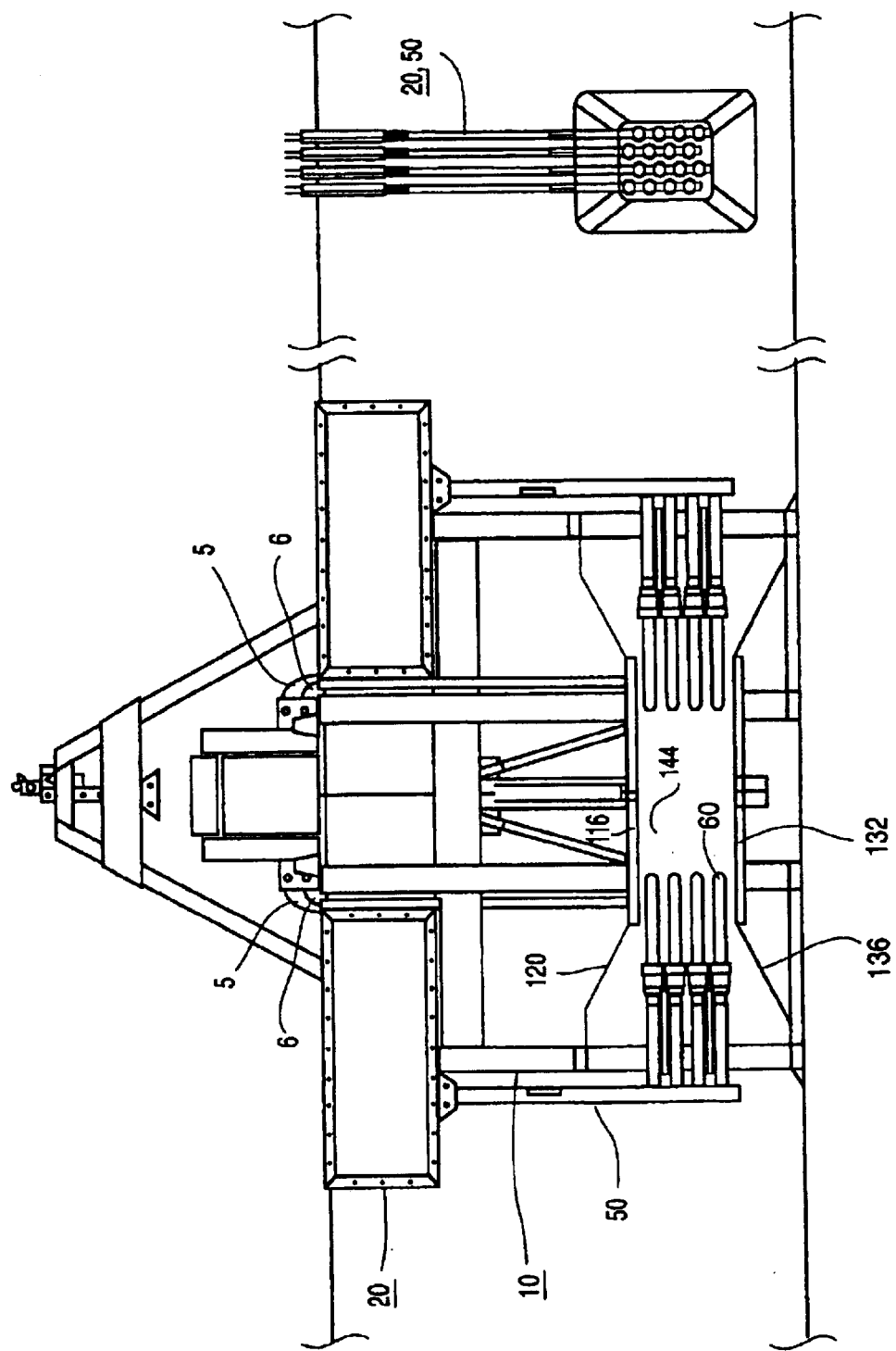

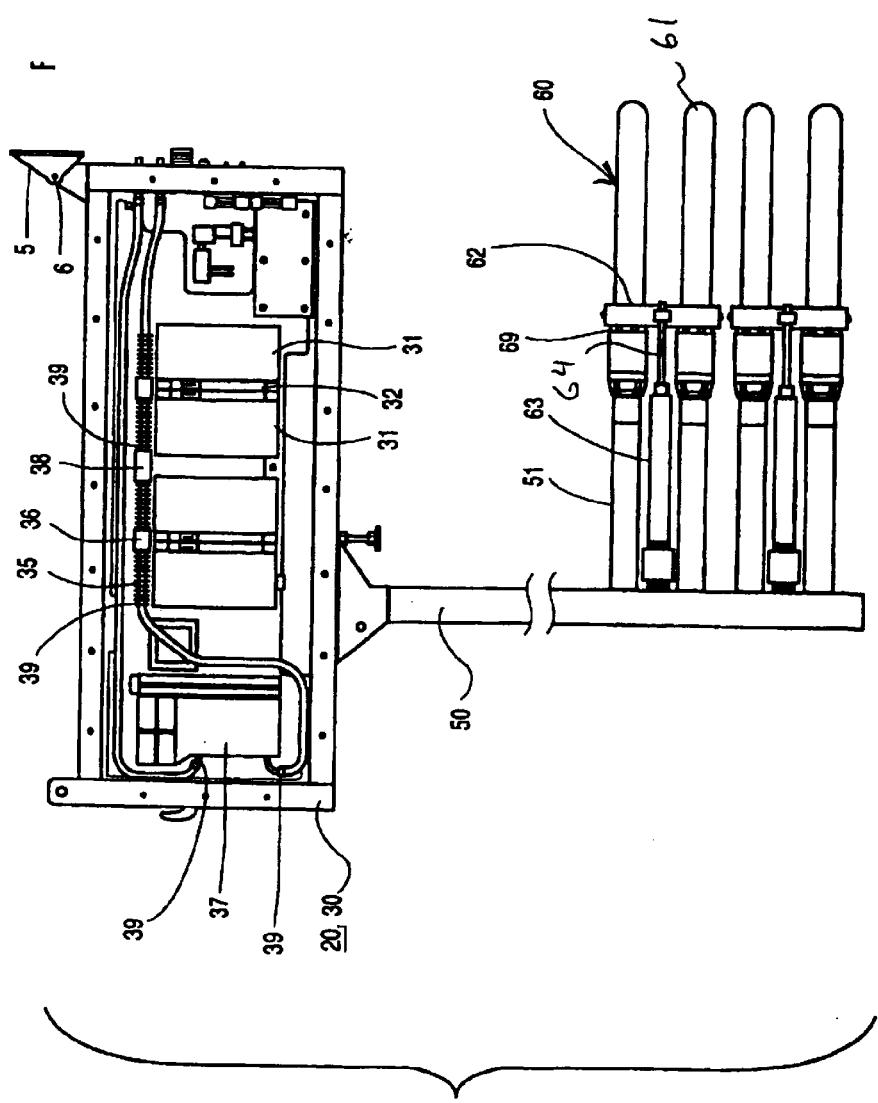

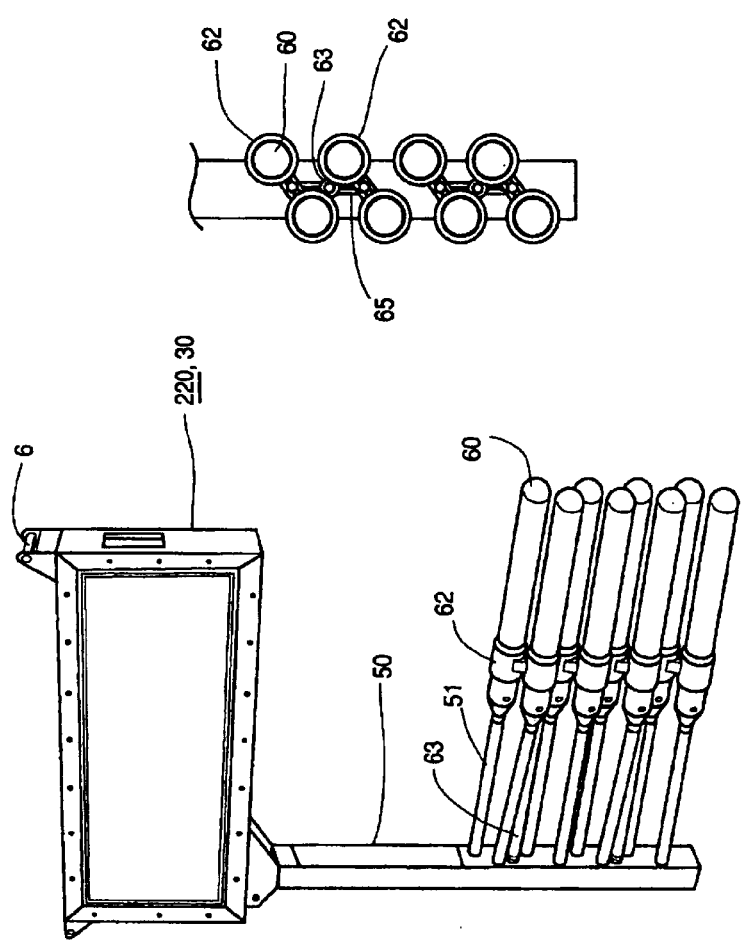

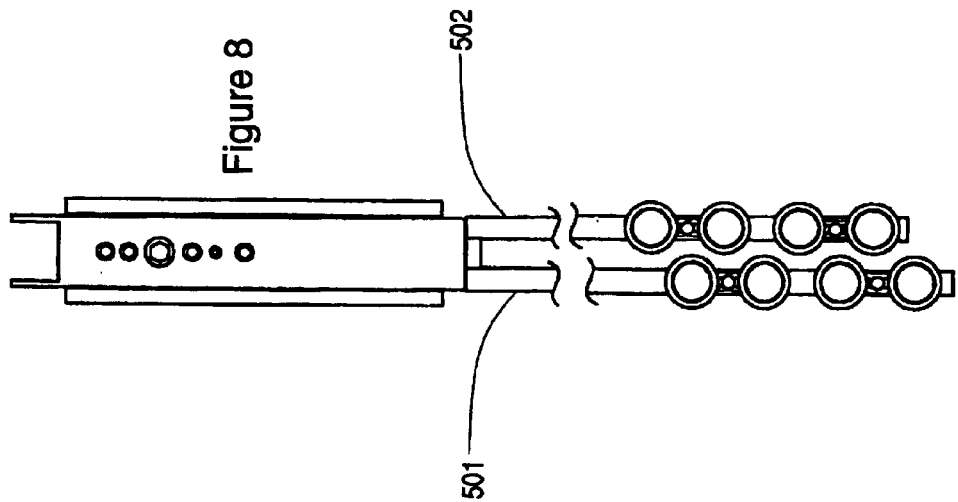
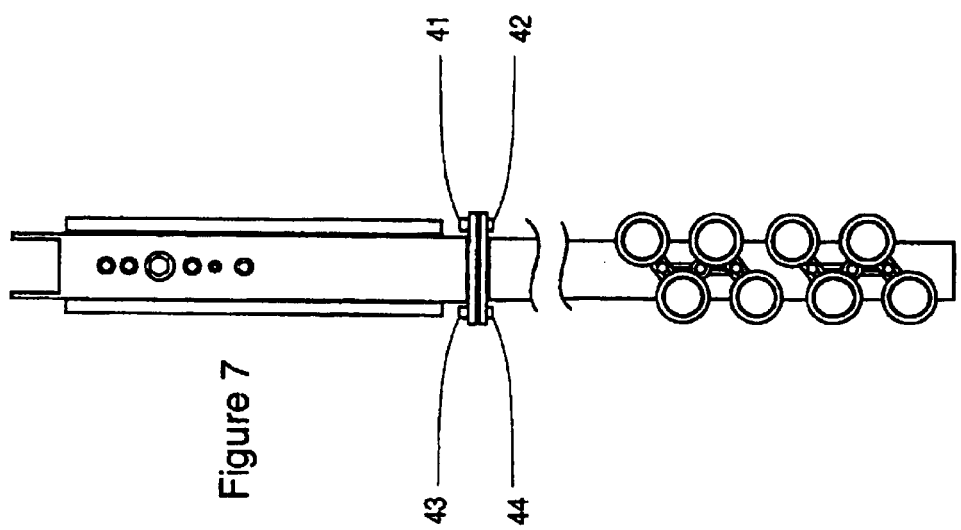

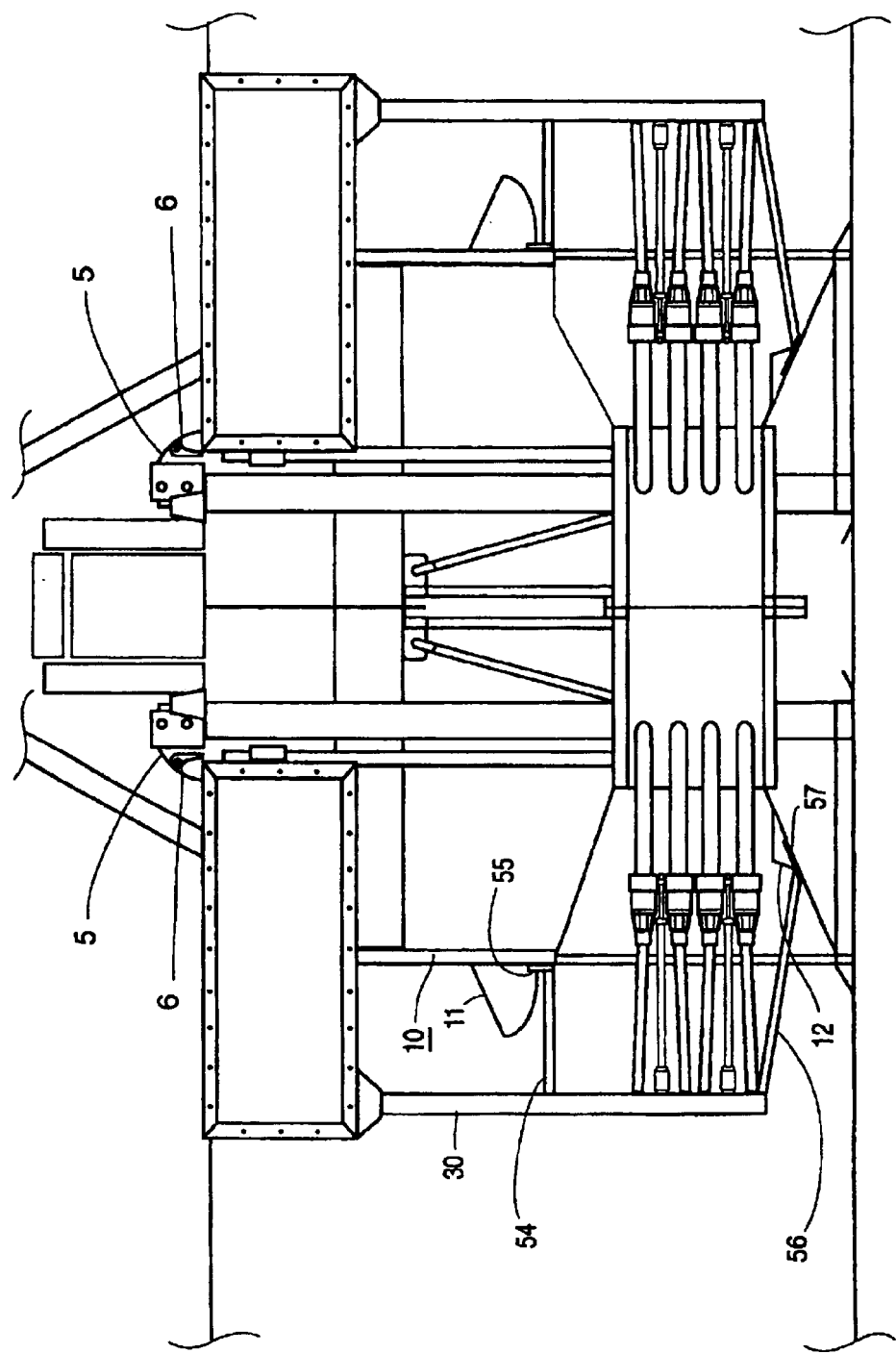

RADIATION SOURCE MODULE

This is a continuation application of application Ser. No. 09/493,226, filed Jan. 28, 2000 now abandoned, the contents of which are incorporated herein by reference.

BACKGROUND OF THE INVENTION

1. Field of the Invention

In one of its aspects, the present invention relates to a radiation source module. In another of its aspects, the present invention relates to a fluid treatment system comprising the present radiation source module.

2. Description of the Prior Art

Fluid treatment systems are known generally in the art.

For example, U.S. Pat. Nos. 4,482,809, 4,872,980 and 5,006,244 (all in the name of Maarschalkerweerd and all assigned to the assignee of the present invention and hereinafter referred to as the Maarschalkerweerd #1 Patents) all describe gravity fed fluid treatment systems which employ ultraviolet (UV) radiation.

Such systems include an array of UV lamp modules (e.g., frames) which include several UV lamps each of which are mounted within sleeves which extend between and are supported by a pair of legs which are attached to a crosspiece. The so-supported sleeves (containing the UV lamps) are immersed into a fluid to be treated which is then irradiated as required. The amount of radiation to which the fluid is exposed is determined by the proximity of the fluid to the lamps, the output wattage of the lamps and the flow rate of the fluid past the lamps. Typically, one or more UV sensors may be employed to monitor the UV output of the lamps and the fluid level is typically controlled, to some extent, downstream of the treatment device by means of level gates or the like.

U.S. Pat. Nos. 5,418,370, 5,539,210 and 5,590,390 (all in the name of Maarschalkerweerd and all assigned to the assignee of the present invention and hereinafter referred to as the Maarschalkerweerd #2 Patents) all describe an improved radiation source module for use in gravity fed fluid treatment systems which employ UV radiation. Generally, the improved radiation source module comprises a radiation source assembly (typically comprising a radiation source and a protective (e.g., quartz) sleeve) sealingly cantilevered from a support member. The support member may further comprise appropriate means to secure the radiation source module in the gravity fed fluid treatment system.

The Maarschalkerweerd #1 Patents and the Maarschalkerweerd #2 Patents represent significant advances in the art. Notwithstanding this, there is still room for improvement. Specifically, in implementation of the fluid treatment systems taught in the Maarschalkerweerd #1 Patents and the Maarschalkerweerd #2 Patents, it is preferred to stagger columns of the radiation sources with respect to one another to maintain a substantially uniform distance between all radiation sources in the array of radiation sources. This serves to maintain a substantially uniform fluid (e.g., water) layer thickness during fluid treatment.

Since the radiation source modules taught in the Maarschalkerweerd #1 Patents and the Maarschalkerweerd #2 Patents are characterized by a single, aligned row of radiation sources per module, there are two design possibilities.

First, the modules may be designed to be identical to one another and vertically staggered with respect to one another to stagger adjacent columns of radiation sources. This necessitates a more complicated design in the fluid treatment system to vertically stagger adjacent modules with respect to one another.

Second, the fluid treatment system design may be simplified to vertically align adjacent radiation source modules in an identical manner. This necessitates having two different module designs for adjacent radiation source modules to present the staggered adjacent columns of radiation sources.

Still further it would be desirable to have an improved radiation source module which, for a given number of radiation sources in an array in a fluid treatment system, would allow for a reduction of the number support members needed compared with the number needed following the teaches of the Maarschalkerweerd #1 Patents and the Maarschalkerweerd #2 Patents.

SUMMARY OF THE INVENTION

It is an object of the invention to provide a novel radiation source module which obviates or mitigates at least one of the above-mentioned disadvantages of the prior art.

Accordingly, in one of its aspects, the present invention provides a radiation source module for use in a fluid treatment system, the module comprising:

a substantially elongate first support member having a longitudinal first axis; and a first pair of radiation source assemblies extending from the first support member, each radiation source assembly comprising a radiation source;

wherein the first pair of radiation source assemblies is oriented such that a second axis extending through a center point of each radiation source assembly is disposed at an angle with respect to the first axis.

In another of its aspects, the present invention provides radiation source module for use in a fluid treatment system, the module comprising:

a substantially elongate first support member having a longitudinal first axis; and a first column of radiation source assemblies extending from the first support member, and a second column of radiation source assemblies extending from the first support member, each radiation source assembly comprising a radiation source;

the first column of radiation source assemblies and the second column of radiation source assemblies disposed adjacent one another.

BRIEF DESCRIPTION OF THE DRAWINGS

Embodiments of the present invention will be described with reference to the accompanying drawings, in which:

FIG. 2 illustrates a side elevation of a commercial embodiment of a prior art fluid treatment system similar to the one taught in the Maarschalkerweerd #2 Patents;

FIG. 3 illustrates a partial front elevation of the fluid treatment system illustrated in FIG. 2;

FIG. 4 illustrates a more detailed side elevation of a radiation source module of the type illustrated in FIG. 1–3; and FIGS. 5–11 illustrate various embodiments of the present radiation source module and a fluid treatment system incorporating same (FIG. 11).

DETAILED DESCRIPTION OF THE PREFERRED EMBODIMENTS

Figure 1:
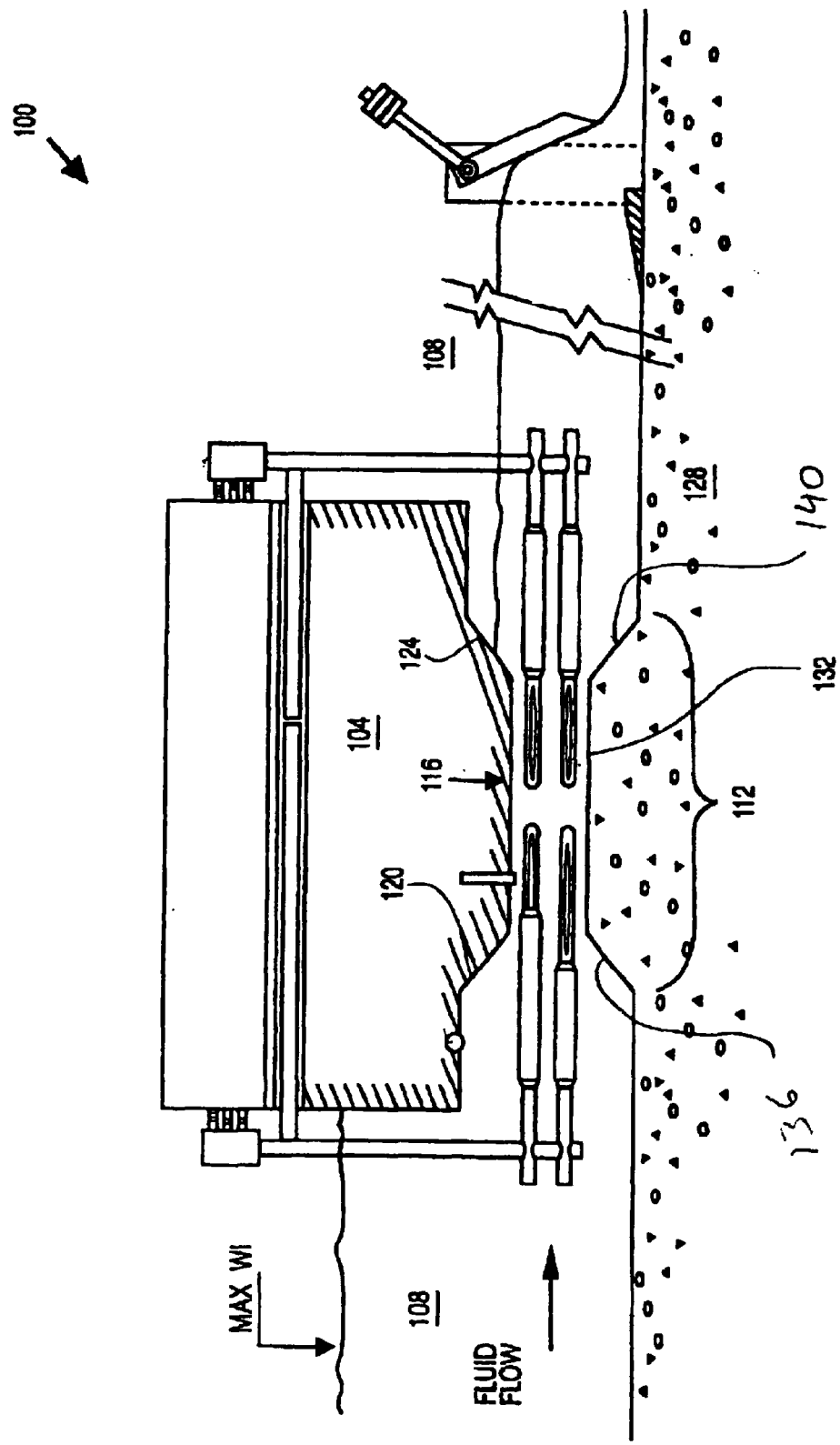
FIG. 1 illustrates a side elevation, in partial cross-section, of a prior art fluid treatment system as taught in the Maarschalkerweerd #2 Patents.

For clarity, a brief description of a prior art fluid treatment device will be presented before discussing the present invention. FIG. 1 illustrates a prior art treatment system as described in U.S. Pat. No. 5,590,390 (one of the Maarschalkerweerd #2 Patents).

Thus, a system 100 includes a main body 104 which is installed across an open fluid canal 108 such that the all of the fluid flow through canal 108 is directed through a treatment zone 112. Main body 104 may be precast concrete, stainless steel or any other material suitable for use with the fluid to be treated and which is resistant to the type of radiation employed.

The lower surface of main body 104 includes a central section 116 which extends downward with leading and trailing inclined sections 120 and 124, respectively. A corresponding upraised central section 132 is located on abase 128 of canal 108 beneath central section 116 and includes leading and trailing inclined sections 136 and 140, respectively. Central section 132 may be part of main body 104 or may be part of base 128 (as illustrated).

FIGS. 2 and 3 illustrate a more detailed commercial embodiment of a system similar to the one illustrated in FIG. 1. Sections 116 and 132 form a narrowed irradiation zone 144, while sections 120 and 136 form a tapered inlet transition region and sections 124 and 140 form a tapered outlet transition region. A plurality of radiation source modules 20 are mounted on the main body, and each module includes a leg 50 with UV lamp assemblies 60 which extend into the irradiation zone 144.

As shown in FIG. 3, a plurality of lamp modules 20 are arranged across the width of the irradiation zone 144 with a spacing between lamp modules 20 which is designed to ensure that the fluid to be treated is irradiated with a predetermined minimum dosage of UV radiation. The lamps are preferably spaced in a triangular configuration as shown to reduce the maximum distance from the lamp to any particle of fluid in the irradiation zone. However rectangular or other lamp configurations are possible.

FIG. 4 shows a lamp module 20 of the device in FIG. 2. The module has an enclosure 30, shown with cover removed, which contains the electronic ballast 31 and other components used to provide the power and control functions to the lamps and the lamp sleeve wipers. The module 20 is attached by a hinge pin 6 to a hinge bracket 5 which is mounted on the frame assembly 10. The ballasts 31 are clamped to mounting bases 32 which are cooled by fluid flowing through internal passages. The ballast 31 is constructed so that the main heat generating components are mounted on a conductive plate which is in proximity to the cooled mounting bases 32. However a significant proportion of the heat is generated by other components which are cooled by air forced through the ballast case by a fan (not shown). Heat is then removed from the air in the ballast enclosure by fins 35 on the coolant pipes 36. Additional heat is removed from the air by a fan powered heat exchanger 37. The cooling components are attached by a series of hoses 38 and clamps 39.

Each module 20 has a leg 50 with a plurality of rigid standoff structures 51 which extend from the leg and support the UV lamp assemblies 60. Each lamp assembly has a lamp mounted inside an outer sleeve 61. A wiper assembly 62 is mounted on each pair of sleeves 61 and a hydraulic cylinder 63 has a rod 64 which extends and retracts to move the wiper assembly 62 along the sleeves 61 and remove any deposits which may diminish the intensity of radiation emitting from the lamp.

While this system has been successful, it suffers from several disadvantages caused by the arrangement of the lamp modules 20 which limits the width of each module. The limited width results in a configuration of mounting the ballasts 31 with a plurality of liquid cooled mounting bases 32, individual finned heat exchangers 39 and an additional cooling device 37 to remove heat from the air inside the enclosure. This configuration requires many separate components and many individual fluid connections which are potential leaks. The transfer of heat from the air in the enclosure is not efficient, resulting in higher operating temperatures which can reduce reliability and the life of the ballasts. The physical constraints of the mounting configuration of the lamp ballast and other components within the module also make initial assembly and routine maintenance of the device relatively labour intensive.

FIG. 5 illustrates the lamp module with the configuration of the new invention. The module 220 carries two columns of lamps 60 and therefore can have an enclosure approximately twice as wide as the prior art module. The preferred configuration shown in FIG. 5 has a single leg 50 with a plurality of standoff extensions 51 which carry the lamps 60 at the desired spacing. The wider single leg 40 with two columns of lamp assemblies 60 has greater rigidity than a narrower leg and also is less costly than two separate legs. In addition, the pattern of the lamps allows one hydraulic cylinder to actuate the cleaning collars of four lamps, reducing the number of hydraulic cylinders 63 and hydraulic lines and fittings (not shown). FIG. 6 shows a partial end view of the lamps, wipers and hydraulic cylinder illustrating two wiper collar assemblies 62 attached by a yoke 65 which is mounted on the rod of the hydraulic cylinder 63.

As illustrated in FIG. 7, an optional feature of this invention is the ability to have the lamp leg detachable from the module enclosure. The ballast enclosure 30 has a flange 41 and the lamp leg 50 has a flange 42. The flanges are joined by bolts 43 and nuts 44. Having separate enclosure and lamp leg assemblies allows each component to be made of different materials. For example, most applications require stainless steel for all components in contact with the fluid in the channel, but other materials such as aluminum may be used for the enclosure. Also, many applications require custom lengths of lamp leg, and separating the lamp leg from the module enclosure reduces inventory and simplifies manufacturing. In addition, having the lamp leg separate from the module enclosure allows repair or replacement of the lamp leg without replacing the module enclosure.

FIG. 8 illustrates an alternative construction with a single ballast enclosure with two single lamp legs 501 and 502. This configuration provides the benefits of improved ballast cooling.

Figure 9:
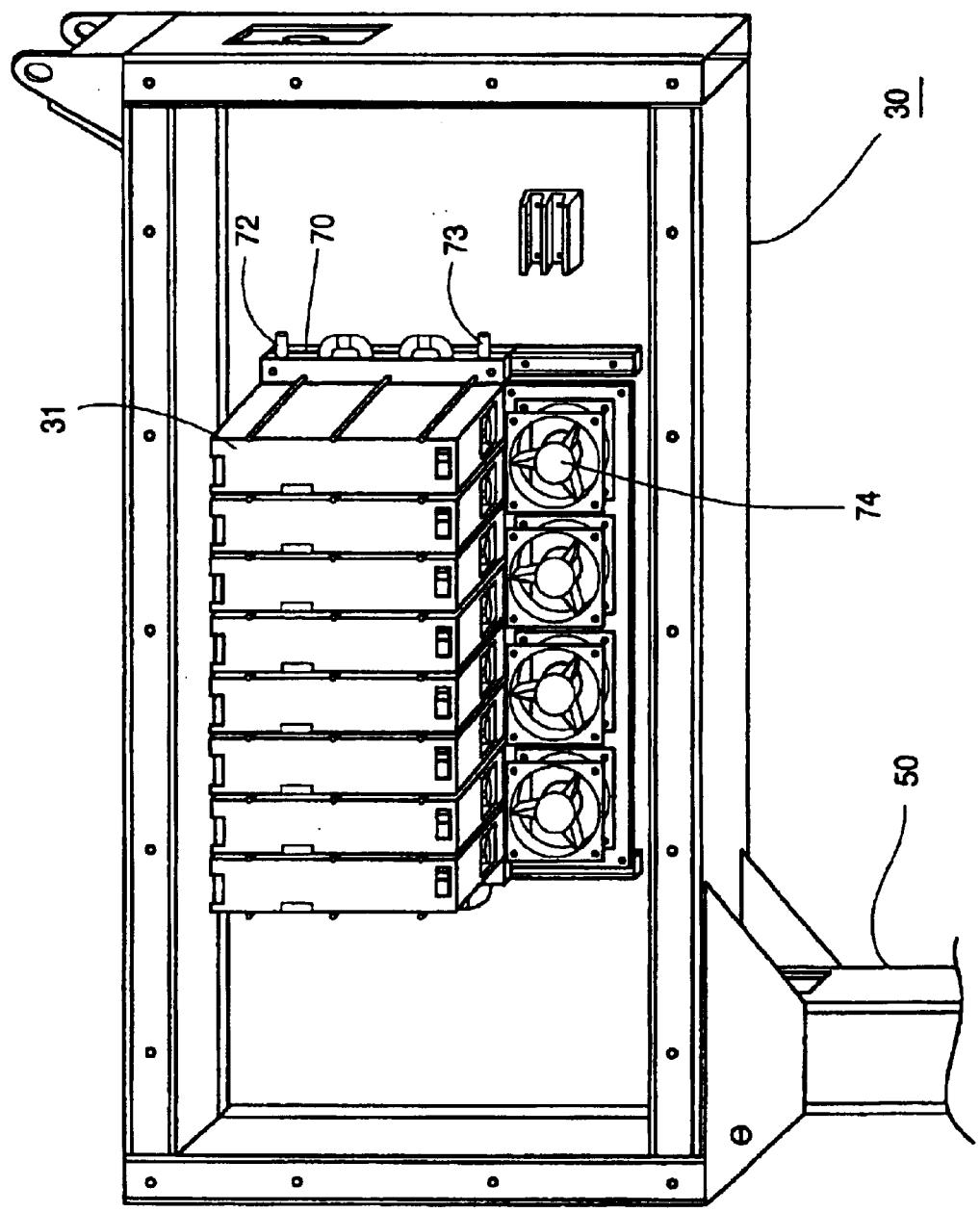

FIG. 9 shows a view of the module enclosure in FIG. 5 with the cover removed. In place of the plurality of liquid cooled mounting structures illustrated in FIG. 4 is a single chilled plate 70 which is cooled by liquid flowing through internal passages. The ballasts 31 are mounted directly to one face of the chilled plate 70 so that the hot mounting base of the ballast is in close proximity to the plate for improved heat transfer.

Figure 10:
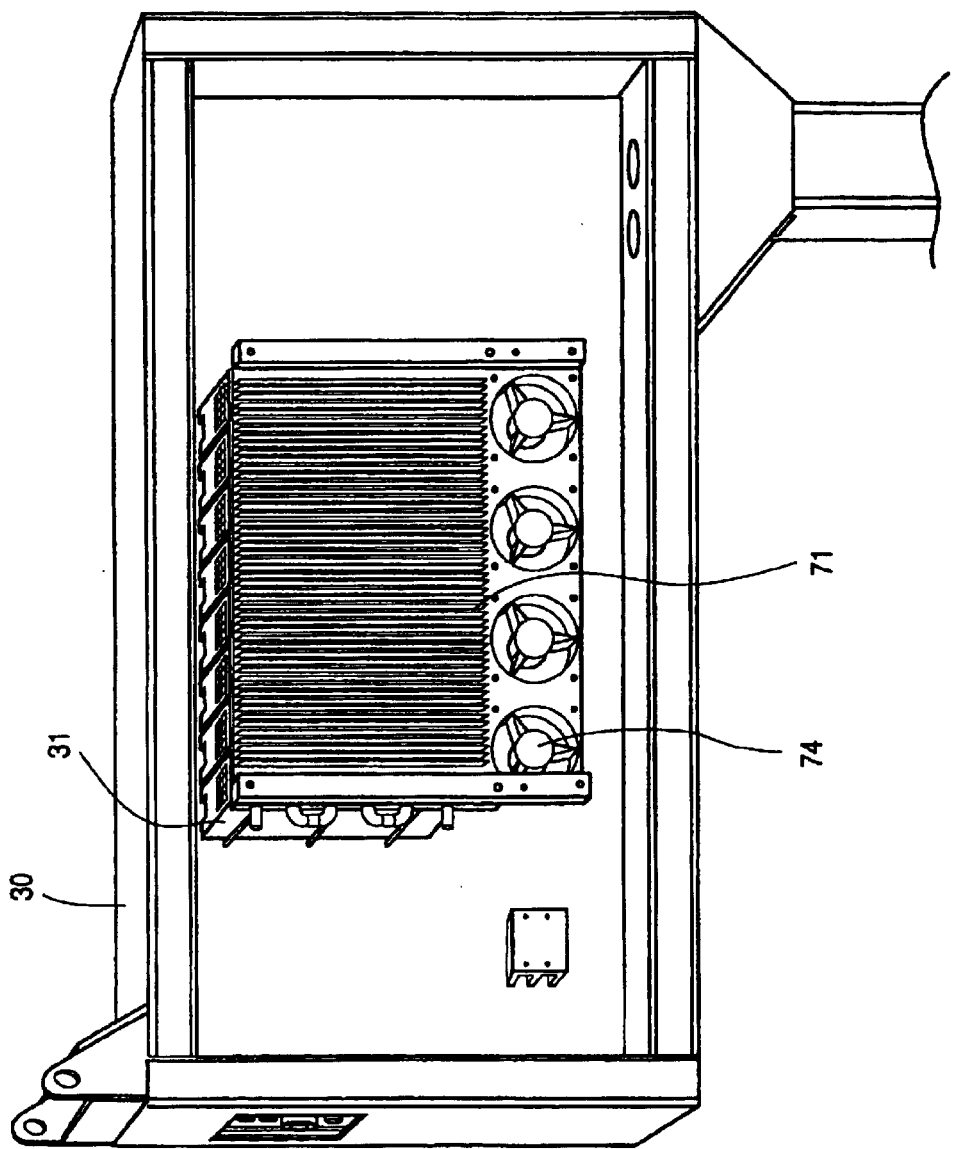

As shown in FIG. 10, a surface of the chilled plate 70 has a plurality of fins 71. The air which is heated by passing through the ballasts is circulated around the chilled plate and past the fins by a fan 74, and heat is transferred from the air through the fins 71 to the chilled plate 70. The new orientation of the ballasts allows easier assembly and maintenance. The chilled plate 70 has only two fluid connections, inlet pipe 72 and outlet pipe 73, and the probability of coolant leaks is greatly reduced. The wider enclosure reduces the total number of modules and enclosures by half, reducing cost and improving maintenance because only half as many covers must be removed for access. Having fewer modules for a given number of lamps also reduces by half the number of hydraulic and electrical connections to the modules, resulting in additional savings.

FIG. 11 illustrates an optional feature to improve the accuracy of positioning the lamps relative to the reactor. The traditional method of mounting the module allowed significant lateral movement of the lamps, particularly with long lamp legs. Accurate positioning of the lamps within the irradiation zone is important to achieve a high degree of efficiency and reliability of disinfection. The positioning arm 54 has a narrow cross section to minimize resistance to fluid flow. The end of the positioning arm has a plate 55 with a tapered notch which engages a plate 11 attached to the inlet or outlet portion of the frame assembly 10, providing accurate lateral positioning. Additional accuracy can be achieved by using a second positioning bar 56 below the bottom lamp, as shown in FIG. 11. The bar 56 carries a plate 57 with a tapered notch which engages a plate 12 attached to the bottom of the inlet or outlet funnel as shown. The plate 12 has a tapered profile to minimize the chance of trapping debris passing through the canal. Because three points define a plane, the hinge and the two positioning bars provide a more rigid mounting with greater resistance to skewing of the lamp than can be provided only by the mounting hinge of the module.

While the present invention has been described with reference to preferred and specifically illustrated embodiments, it will of course be understood by those skilled in the art that various modifications to these preferred embodiments and illustrated embodiments may be made without departing from the spirit and scope of the invention. For example, while the specific cleaning system illustrated is one having a cleaning ring to provide a combined chemical/mechanical cleaning action, it is of course possible to modify this design to utilize, for example, a mechanical cleaning system. Further, since the present radiation source module allows for the use of a relatively wider support leg, this facilitaes installing a power supply (e.g., a ballast) within or attached to the support leg to facilitate improved cooling of the power supply by immersion in the fluid being treated. Still further, while the illustrated embodiments depict a single drive cylinder effecting cleaning of four surrounding cleaning rings, those of skill in the art will appreciate that the design may be modified to drive any number of cleaning rings (i.e., less than or greater than four cleaning rings), preferably in multiples of 2. Still further, it is possible to modify the illustrated radiation source module such that the radiation source assemblies have a non-perpendicular cantilevered orientation with to the support leg. One skilled in the art will also appreciate that it is possible to dispose a plurality of stand-off extensions on opposite sides of the single support leg. This would allow for adjustability of the spacing between adjacent radiation sources and would be particularly advantageous (but not limited to) when adopted in a design similar to the Maarschalkerweerd #1 Patents. Still, the stand-off extensions 51 may design to be of differing lengths to allow of axial staggering of the radiation sources in a given array. Other modifications which do not depart from the spirit and scope of the present invention will be apparent to those of skill in the art.

All publications, patents and patent applications referred to herein are incorporated by reference in their entirety to the same extent as if each individual publication, patent or patent application was specifically and individually indicated to be incorporated by reference in its entirety.

What is claimed is:

1. A radiation source module for use in a fluid treatment system, the module comprising:
   a substantially elongate first support member having a longitudinal first axis; and
   an array of radiation source assemblies comprising at least two pairs of radiation source assemblies connected to the first support member, each radiation source assembly comprising a radiation source;
   wherein: (i) each pair of radiation source assemblies is oriented such that a second axis extending through a center point of each radiation source assembly in the pair is disposed at an acute angle with respect to the first axis, and (ii) two adjacent pairs of radiation source assemblies, each pair of radiation source assemblies comprising a radiation source assembly disposed at a substantially uniform distance from three adjacent radiation source assemblies.

2. The radiation source module defined in claim 1, wherein the angle is about 90°.

3. The radiation source module defined in claim 1, wherein the angle is an acute angle.

4. The radiation source module defined in claim 1, wherein a plurality of pairs of radiation source assemblies extend from the first support member.

5. The radiation source module defined in claim 1, wherein the radiation source assemblies are cantilevered from the first support member.

6. The radiation source module defined in claim 1, wherein the radiation source assemblies are cantilevered from the first support member in a substantially non-perpendicular manner.

7. The radiation source module defined in claim 1, further comprising a substantially elongate second support member spaced from the first support member, the radiation source assemblies being supported by both the first support member and the second support member.

8. The radiation source module defined in claim 1, wherein the first radiation source assembly and the second radiation source assembly are in a substantially parallel relationship with respect to one another.

9. A fluid treatment device comprising at least one radiation source module as defined in claim 1.

10. The radiation source module defined in claim 1, wherein the radiation source assemblies each comprise at least one radiation source disposed with a protective sleeve.

11. The radiation source module defined in claim 10, wherein the protective sleeve comprises a quartz sleeve.

12. The radiation source module defined in claim 1, further comprising a first elongate connector between the first support member and a first radiation source assembly, and a second elongate connector between the first support member and a second radiation source assembly.

13. The radiation source module defined in claim 12, wherein the first elongate connector and the second elongate connector are in a substantially non-parallel relationship with respect to one another.

14. The radiation source module defined in claim 13, wherein the first elongate connector and the second elongate connector are of substantially the same length.

15. The radiation source module defined in claim 13, wherein the first elongate connector and the second elongate connector are of a different length.

16. The radiation source module defined in claim 1, further comprising a power supply for the radiation source assemblies.

17. The radiation source module defined in claim 16, wherein the power supply is disposed in a housing attached to the first support member.

18. The radiation source module defined in claim 16, wherein the power supply is disposed in the first support member.

19. The radiation source module defined in claim 1, further comprising a cleaning system for removing fouling materials from an exterior of the radiation source assemblies.

20. The radiation source module defined in claim 19, wherein the cleaning system comprises: (i) a cleaning ring for engagement with a portion of the exterior of the radiation source assemblies, and (ii) motive means to translate the slidable member over the exterior of the radiation source assembly.

21. The radiation source module defined in claim 20, wherein a single motive means is provided for at least two radiation source assemblies.

22. The cleaning apparatus defined in claims 20, wherein the cleaning ring comprises a chamber for surrounding a portion of the exterior of the radiation source assembly.

23. The cleaning apparatus defined in claim 22, wherein the cleaning ring further comprises an inlet for introduction of a cleaning solution to the chamber.

24. The radiation source module defined in claim 20, wherein at least two pairs of radiation source assemblies extend from the first support member to define a quartet of radiation source assemblies.

25. The radiation source module defined in claim 24, wherein single motive means is provided for the quartet of radiation source assemblies.

26. A radiation source module for use in a fluid treatment system, the module comprising:

a substantially elongate first support member having a longitudinal first axis; and a first column of radiation source assemblies connected to the first support member, and a second column of radiation source assemblies connected to the first support member, each radiation source assembly comprising a radiation source;

the first column of radiation source assemblies and the second column of radiation source assemblies disposed adjacent one another, an axis passing through a radiation source assembly in the first column and a corresponding radiation source assembly in the second column defining an acute angle with respect to the first axis;

wherein each radiation source assembly is disposed at a substantially uniform distance from three adjacent radiation source assemblies.

27. The radiation source module defined in claim 26, wherein the first column of radiation source assemblies and the second column of radiation source assemblies are disposed in a substantially staggered relationship with respect to one another.

28. The radiation source module defined in claim 26, wherein the radiation source assemblies are cantilevered from the first support member.

29. The radiation source module defined in claim 26, further comprising a substantially elongate second support member spaced from the first support member, the radiation source assemblies being supported by both the first support member and the second support member.

30. A fluid treatment device comprising at least one radiation source module as defined in claim 26.

31. The radiation source module defined in claim 26, wherein the radiation source assemblies each comprise at least one radiation source disposed with a protective sleeve.

32. The radiation source module defined in claim 31, wherein the protective sleeve comprises a quartz sleeve.

33. The radiation source module defined in claim 26, further comprising a first elongate connector between the first support member and a first radiation source assembly, and a second elongate connector between the first support member and a second radiation source assembly.

34. The radiation source module defined in claim 33, wherein the first elongate connecter and the second elongate connector are in a substantially nonparallel relationship with respect to one another.

35. The radiation source module defined in claim 34, wherein the first radiation source assembly and the second radiation source assembly are in a substantially parallel relationship with respect to one another.

36. The radiation source module defined in claim 26, further comprising a power supply for the radiation source assemblies.

37. The radiation source module defined in claim 36, wherein the power supply is disposed in a housing attached to the first support member.

38. The radiation source module defined in claim 36, wherein the power supply is disposed in the first support member.

39. The radiation source module defined in claim 26, further comprising a cleaning system for removing fouling materials from an exterior of the radiation source assemblies.

40. The radiation source module defined in claim 39, wherein the cleaning system comprises: (i) a cleaning ring for engagement with a portion of the exterior of the radiation source assemblies, and (ii) motive means to translate the slidable member over the exterior of the radiation source assembly.

41. The radiation source module defined in claim 40, wherein a single motive means is provided for at least two radiation source assemblies.

42. The cleaning apparatus defined in claim 40, wherein the cleaning ring comprises a chamber for surrounding a portion of the exterior of the radiation source assembly.

43. The cleaning apparatus defined in claim 42, wherein the cleaning ring further comprises an inlet for introduction of a cleaning solution to the chamber.

44. The radiation source module defined in claim 40, wherein at least two pairs of radiation source assemblies extend from the first support member to define a quartet of radiation source assemblies.

45. The radiation source module defined in claim 44, wherein single motive means is provided at least for each quartet of radiation source assemblies to define a quartet of radiation source assemblies.

* * * * *